United States Patent [19]

Feldmann

[11] 4,152,122
[45] May 1, 1979

[54] APPARATUS FOR THE PRODUCTION OF METHANE CONTAINING GAS BY HYDROGASIFICATION

[75] Inventor: Herman F. Feldmann, Worthington, Ohio

[73] Assignee: Syngas International, Ltd., Oklahoma City, Okla.

[21] Appl. No.: 857,516

[22] Filed: Dec. 5, 1977

[51] Int. Cl.$^2$ .............................. C10J 3/48; C10J 3/56
[52] U.S. Cl. ......................................... 48/111; 202/99
[58] Field of Search ...................... 48/197 A, 209, 210, 48/111; 201/25; 202/99

[56] References Cited

U.S. PATENT DOCUMENTS

| | | | |
|---|---|---|---|
| 3,733,187 | 5/1973 | Feldmann | 48/209 |
| 3,736,111 | 5/1973 | Gardner et al. | 48/111 |
| 3,736,233 | 5/1973 | Sass et al. | 48/210 |
| 3,782,913 | 1/1974 | Donatl | 48/210 |
| 3,985,519 | 10/1976 | Kaling et al. | 48/210 |
| 4,005,994 | 2/1977 | Feldmann | 48/209 |
| 4,077,847 | 3/1978 | Cloi et al. | 48/111 |

*Primary Examiner*—S. Leon Bashore
*Assistant Examiner*—Peter F. Kratz
*Attorney, Agent, or Firm*—Sidney W. Millard; Gerald L. Smith

[57] ABSTRACT

An improved system for producing methane-containing product gas by the hydrogasification process. With the system, solid municipal waste is comminuted and dried following which it is introduced to the lock hopper receivers for transference to an elongate hydrogasification reactor. Synthesis gas is introduced to a lower region of the reactor and the comminuted waste, including inorganic materials, is dried and converted to methane-containing product gas and char. The char is removed from the system by a variety of separation systems including cyclone separators or aspirators and the inorganic fractured waste materials pass through the reactor but are undamaged and in a sterile condition ideally suited for recovery. A gasification reactor is incorporated with the system which receives char from the process as well as oxygen to produce the synthesis gas utilized in the hydrogasification reactor. Where no inorganic materials are present, the organic materials may be introduced both to the gasification reactor to produce synthesis gas as well as to the hydrogasification reactor to produce char end product gas. The char is removed from the product gas and returned to the synthesis gas producing gasification reactor. Drying may be carried out utilizing a fluidized sand bed drying technique.

25 Claims, 7 Drawing Figures

APPARATUS FOR THE PRODUCTION OF METHANE CONTAINING GAS BY HYDROGASIFICATION

BACKGROUND

Recently, principal population centers on the North American continent and elsewhere have experienced such severe shortages of natural gas, that industrial performance has been reduced, educational institutions have been closed under severe cold weather conditions and general business entities have witnessed a lowering in employee efficiency and performance under emergency gas conservation operating conditions. For several years, the home construction industry has been required to provide electrical energy to the exclusion of gas derived energy, thus imposing significantly higher living costs on the purchasers of new homes. While exploration for new sources of natural gas can be encouraged through financial incentives and the like, expectations of major finds at sites available to the Western world are not enthusiastic. Consequently, secondary gas resources known to be available have been given considerable attention.

Those concerned with the development of additional natural gas sources have not lost sight of the potential for converting available carbon resources to a product gas suitable as a natural gas supplement or substitute. Coal gasification long has been the subject of study. Of more current interest, however, are efforts to convert the ever increasing volumes of solid wastes of municipalities and industries to a usable gas. The direct application of coal gasification processes to lowbulk density, fibrous, low-ash feed materials like solid waste, manure and other forms of biomass is not likely to be successful because of the vast difference in physical properties between coal and these other cellulosic feed stocks. For example, most coal gasification processes employ fluid beds in which coal char is the fluidized solid. However, because of the very low bulk density of solid waste and biomass type materials and in view of their fibrous nature, they will tend to excessively elutriate from any reactor of a conversion system unless very low superficial gas velocities are used in conjunction with the systems. Low gas velocities require low throughput rates which, in turn, result in increased capital requirements for gasifiers and like components of any conversion system. For example, in the production of an intermediate - Btu gas from the low-sulfur feeds where $H_2S$ removal is not necessary, the gasifier of such system is a large fraction of the total capital investment and thus the economics of any conversion system for these fibrous materials are greatly affected by variations in reactor throughput rates. While organic materials, per se, may range broadly from diamonds to common garbage, the types of materials contemplated for the instant conversion systems are those generally falling within the low bulk density fibrous material category principally including solid waste and biomass. Solid waste will include such materials as manure and municipal waste, while biomass is considered generally to encompass such materials as bagasse, energy crops, seaweed including kelp, cornstalks, forest residue and general plant residues.

A variety of technical approaches have been proposed in attempting the conversion of solid waste and biomass to product gas. For example a synthetic natural gas may be developed from solid municipal waste by controlled biodegradation. However, facilities having an extremely large vessel capacity operating on long solid waste residence intervals are required for carrying out such techniques. Additionally, the by-product from such systems may not be desirable and may represent a disposal problem in and of itself. Further, inorganic constituents of the waste material generally are required to be removed before the waste is introduced to the digestive process.

Another conversion technique, described, for example, in U.S. Pat. Nos. 3,729,298 and 3,817,724, seeks to develop a product gas from solid waste by pyrolysis, a system wherein the hydrocarbon solids of the waste material are subjected to relatively high temperatures to generate a methane-containing gas, as well as a relatively high quantity of tar and char.

Certain disadvantages accrue with the use of the pyrolysis procedure, the more apparent being the disposal problem for the residue and another residing in a requirement for developing the heat or thermal energy to create the pyrolysis reaction to generate product gas. For this, generally, about twenty percent of the product gas itself is drawn off from the process to generate the heat energy required. A similar approach is provided in U.S. Pat. No. 3,874,116 in which heat is supplied to the zone producing combustible gases through the burning of a portion of recycled synthesis gas. For either approach, the thermal energy demand is significant, temperatures in the range of 1700° F. and up being required to be generated within the reactor. As another aspect of these systems, at such higher temperatures, should the developed product methane enter the gasification zone of the reactor, it will tend to combine with water present as steam to break down to carbon monoxide and hydrogen gas, thus leading to further losses in output efficiency. Higher temperatures pose another requirement to the systems in that the inorganic components of the solid waste material, i.e. aluminum, glass, steel and other products should be removed prior to the introduction of waste to the reactor. This follows, inasmuch as such materials have an important recovery value in and of themselves and, if subjected to the higher temperatures of the pyrolysis reaction, will tend to break down to less desirable forms, as well as represent substances using up volume while remaining inert within the chemical process.

Another conversion technique to which the instant invention is particularly addressed, involves a process conventionally referred to as hydrogasification. Generally, the hydrogasification reaction is one wherein the carbon component of the waste material is reacted with hydrogen-containing synthesis gas to produce methane. The temperature at which this reaction occurs is one relatively lower, for example, than that required for the gasification reaction, hydrogen gas generally being introduced to the reaction at about 1000° F. As described in U.S. Pat. Nos. 3,733,187 and 4,005,994, the hydrogasification process is one wherein solid waste refuse is shredded and introduced into a confined pressurized zone which is generally elongate in nature and vertically oriented. As the waste material is introduced at the top of the zone, a hot, hydrogen-containing synthesis gas is introduced at the lowermost regions thereof. As the waste material migrates under gravitational force downwardly through the zone, this moisture content thereof is removed and upon complete removal of the moisture, the methane-producing hydrogasification reaction occurs and the organic material subsequently becomes a carbon containing char. This char then is moved to a gasification reactor at which location it is substantially entirely converted to hot synthesis gas in the presence of oxygen and steam and, by virtue of the exothermic nature of that reaction, thermal energy is evolved at the levels required in the hydrogasification zone. Advantageously, only a minor amount of residue requiring disposal is developed as a by-product of the synthesis gas production process. As described in the noted U.S. Pat. No. 4,005,994, a highly efficient utilization of thermal energy with the process is availed. Further, a subsidiary advantage ensues with the hydrogasification process due to the relatively lower temperatures developed within the reaction zone of the hydrogasifier. With the system, both inorganic as well as organic waste components may be introduced into the reactor. These inorganic components pass by gravity through the reactor and are subjected to temperatures which advantageously provide for their sterilization while being of such lower level as to prevent their destruction as by the sintering of glass or oxidation breakdown of metals. At the lowermost region of the hydrogasification reactor zone, the inorganic material readily may be recovered as a valuable by-product, thus enhancing the economic feasibility of this form of product gas production. While the theory and lesser scale demonstration of all of the above synthetic gas production systems has been demonstrated, practical implementation thereof accommodating those volumes of municipal waste required to be treated has not been effected without difficulty. A pyrolysis system installed in Baltimore, Maryland met with severe operational difficulties due to a variety of practical imperfections, for example as associated with the pretreatment, movement and storage of waste raw material as well as with the reactor related manipulation thereof.

Because the gas production systems should be located near their source of raw material as well as near gas distribution networks, i.e. near major population centers, they must retain a capability for accepting large volumes of waste and accommodating these volumes without creating odor and pollution nuisances. Necessary storage of the material should be of so short a residence interval as to be without significant odor nuisance. Further, the production of unwanted, polluting by-products such as tars and the like should be minimized.

In view of the significant capital expenditure represented with any given gas production installation, the necessary overall size of the facility must remain as practical in scope as possible. For further practical necessity, gas impurities, i.e. volatile constituents which necessarily may be generated in conjunction with desired methane production must be minimized and the final synthetic gas product both should be compatible with natural gas supplies as well as must be produced evidencing a relatively constant chemical makeup or consistency.

SUMMARY

The present invention is addressed to a system, method and apparatus providing for the production of methane-containing gas by the hydro-gasification process with enhanced practicality and efficiency. System efficiency is developed through the utilization of generated thermal energy to pretreat waste and/or biomass material as well as in conjunction with the provision of unique pressurized reactor zone drying techniques. The resulting efficiencies permit an advantageous lessening of the physical lengths of vertically oriented reactor zones while improving the thermal efficiency and gas product consistency of the entire system.

In one inventive approach, the confined, pressurized zone of a hydrogasification reactor is provided having explicit drying and hydrogasification regions, the former being located above the latter. Intermediate these regions and at their juncture, a perforate distribution component is provided which, while permitting the gravitationally induced passage of inorganic waste along the entire zone, serves to retain the lighter, moisture-containing organic designated waste within a product gas supported fluidized bed environment. This environment permits an ideal drying time with a minimum of reactor structure volume. Collection conduits leading from the top level of the fluidized bed to the lower reactor region provide for movement of sufficiently dry organic waste for product gas and char development. With this approach, the rate and pressure of synthesis gas introduction to the reaction region of hydrogasification is controlled to achieve the noted fluidized bed type drying performance while permitting gravitational flow of inorganic material into byproduct recovery facilities.

In another aspect and approach, a system is provided wherein hot synthesis gas as well as comminuted or shredded waste are simultaneously introduced at the lowermost region of an elongate pressurized, confined zone. The hot synthesis gas is inserted within the zone at such a rate and pressure as to establish a fluidized bed containing fractured inorganic materials such as glass through which the organic waste components such as paper and the like flow upward. Since the silica-containing glass fragments are characterized in having high specific heat values, a resultant highly efficient heat transfer with commingled moist organic material is achieved. As the organic material dries it migrates upwardly through the zone along with glass particles and, at such time as it is fully dried, reacts with the synthesis gas to produce methane, which reaction occurs under relatively short residence interval periods as compared to that interval required for removal of moisture. Fluidized bed migrating glass particle type inorganic material then overflows through stand pipes as it is replaced by crushed glass from the entering stream of shredded waste. Material thus collected at the upper level of the bed is removed for profitable disposal, while both product gas and char developed during hydrogasification are taken from the top of the zone and separated, for instance, utilizing a cyclone separator. The char then is directed to a gasification zone for use in the production of hot synthesis gas, while the product gas is scrubbed, and, if desired, methanated and conveyed to a distribution network. As an advantageous characteristic of the above system, volatile constituents are cracked in the course of the movement through the elongate singular zone and are converted to simple gases or methane, the system thereby deriving a higher quality product gas.

The elongate zone arrangement of the invention also may utilize a synthesis gas input flow rate not selected to establish a fluidized bed relationship with fractured glass particles and the like but which does promote upward migration of organic materials deposited in the vicinity of the point of introduction of the synthesis gas. Here, as before, the advantageous cracking of volatile constituents is realized and both product gas and char are taken from the top of the reactor confined zone for segregation, while inorganic materials move directly to a collecting quench receptacle.

In another aspect, the invention provides a unique drying station in combination with a hydrogasification reaction arrangement. This drying station permits a significant lowering of reactor size or scope. More particularly, a drying station is utilized wherein solid bulk waste is positioned with metal cages which then are suspended within a hot air fluidized sand bed for an interval selected to assure substantial removal of moisture. Thermal energy imparted to the air utilized in generating the fluidized bed is derived from the product gas itself as it is removed from the smaller scale hydrogasification reactor. As a consequence, more efficient use of thermal energy is provided in combination with smaller and more utilitarian reactor structure.

In each of the embodiments described above, improved system performance may be achieved through the utilization of a particulate, inert, non-abrading and thermally stable material such as alumina within the gasifying synthesis gas producing reactor. This material tends to develop constant temperature throughout the reaction zone thereof and to improve the distribution of char particles within the zone of reaction.

Another embodiment of the invention provides a system and process for producing methane rich gas from waste which is substantially free of inorganic material. Such waste predominantly is present as manure from feed lots and the like and for the instant purpose, represents a highly reactive substance as opposed to typical municipal waste. The system includes serially coupled gasification and hydrogasifying reactors into which manure is fed from two separate feed positions. Because the waste material is substantially free of inorganic components, the temperature established for the gasification reactor as well as that established for hydrogasification advantageously, may be higher. Among the inorganic material free materials which may be utilized in this embodiment in addition or substitution for manure are biomass materials including energy crops, seaweed such as kelp algae, general plant residue such as bagasse, corn stalks, forest residues and the like. In a preferred embodiment, each of the reactors operates in conjunction with a chemically inert, thermally stable and substantially non-abrading particulate material, such as alumina, to improve performance.

In another embodiment of the invention a serial coupling of gasification and hydrogasifying reactors is provided as described immediately above. However, conventional municipal waste including inorganic components is loaded in conjunction with synthesis gas into the hydrogasifying reactor, whereupon product gas char and crushed glass are removed and segregated in two separation steps. The separated char is introduced through a discrete input initially at atmospheric pressure to the gasifying reactor to create synthesis gas. As above, an inert, non-reactive and substantially non-abrading particulate material such as alumina may be used within each of the reactors to improve the performance thereof. In another embodiment of the invention, the glass components of municipal waste are comminuted or shredded following which the metal components are separated therefrom by conventional means. The resultant shredded waste then is introduced into a hydrogasifying reactor. Within the reactor, a fluidized bed of alumina particles is provided through which the waste, entrained within hot synthesis gas migrates. The glass particles within the waste are further fractured and char product gas and such crushed gas are elutriated or moved from the hydrogasifying reactor for submittal to separation stages.

The invention, accordingly, comprises the system, apparatus and method which are exemplified in the following detailed disclosure.

For a fuller understanding of the nature and objects of the invention, reference should be had to the following detailed description taken in connection with the accompanying drawings.

DETAILED DESCRIPTION

Figure 1:
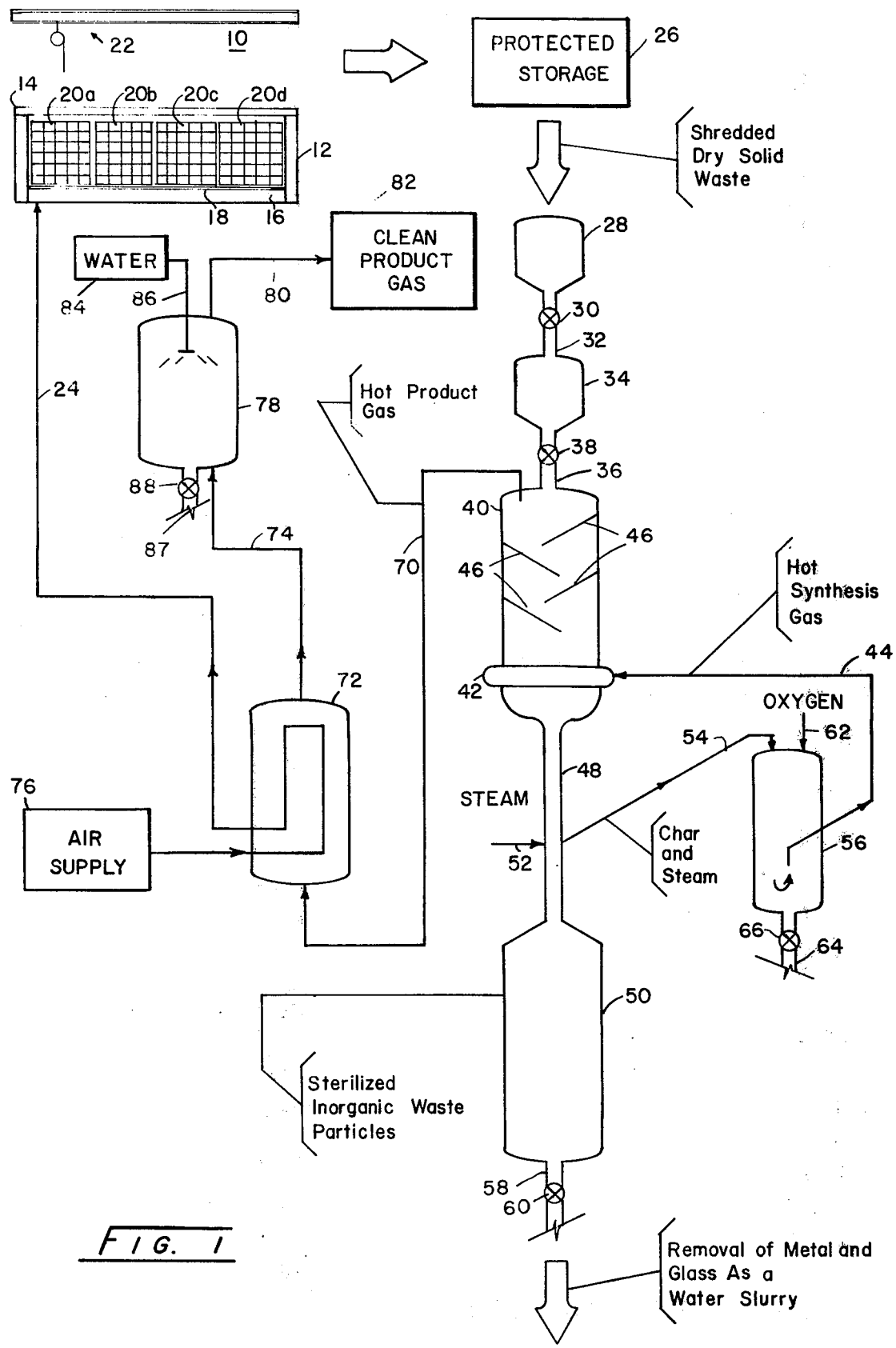
FIG. 1 is a schematic representation of the system and process of one aspect of the invention showing certain components in non-scale flow diagrammatic fashion.

As will become more apparent as the instant description unfolds, the hydrogasification process of the invention is one offering advantages not only in required facility size or scale, but also in providing a better methane containing end product. For example, no pre-separation of reasonably sized inorganic components of the waste, i.e. metals and glass, is required as a precursor step in the system. In fact, with one teaching of the instant invention, a unique utilization of fractured glass components is provided. Next, higher yields of methane are produced with the hydrogasification system than are possible by the alternate technological techniques discussed hereinabove. Further, gas is produced at proper pressures for purification, and a relatively small volume of residue requiring disposal follows from the process. Of particular economic advantage, the recycle value of the metal and glass passing through the system in the course of producing methane-containing gas is uniquely preserved, if not enhanced, inasmuch as no oxidation or sintering of such material occurs while sufficient heat is applied to effect their degreasing and sterilization. An informative background discussion of the hydrogasification process is provided in the above-noted U.S. Pat. Nos. 4,005,994 and 3,733,187 and these patents are incorporated herein by reference for such purposes. The former of the references describes that it is advantageous to separate the methane production reactor from the gasifier reactor in which a hydrogen containing synthesis gas is produced. Generally, the methane production reactor incorporates a confined, vertically oriented zone which is maintained under pressure and wherein introduced solid waste is contacted with the hydrogen containing synthesis gas to react to form methane and a carbonaceous residue, referred to conventionally as "char". This char then is delivered to the gasification reactor where it is combined with oxygen and steam to generate additional synthesis gas is exothermic fashion for reintroduction to the confined, pressurized zone of the hydrogasification reactor. Preferably, the degree of carbon conversion of the waste material within the hydrogasification reactor is controlled to remain below a critical level to insure the availability of sufficient carbonaceous char for delivery to the synthesis gas producing gasification reactor. Where proper control is provided, the synthesis gas produced at the reactor will have adequate heat value to bring the solid waste within the hydrogasification reactor to proper reaction temperatures for generating methane. If properly controlled, essentially all of the char is consumed in the process of developing synthesis gas, however, variations of operational parameters will, in turn, vary output in accordance with the desires of the operator. Generally, however, it has been found that the confined zone of the hydrogasification reactor should remain at a pressure of about 18 atmospheres and that synthesis gas should be introduced thereto at temperatures sufficient to maintain the methane production reactor, i.e. in the area of about 1000° F. At such temperatures, steam passing through the zone will tend to form additional hydrogen and, importantly, will not react with the generated methane to form unwanted carbon monoxide, however, it will react with carbon monoxide within the zone to advantageously produce hydrogen and carbon dioxide.

Referring now to FIG. 1 a first embodiment of the system of the invention is schematically revealed. Solid waste containing both inorganic and organic designated components is delivered to a receiving facility whereupon it is initially shredded and submitted to a drying stage, represented generally at 10. Stage 10 is formed of one or a plurality of vaults as at 12, each having an upwardly disposed access door 14. The vault extends in somewhat lengthwise fashion over a lower-disposed plenum chamber 16. Chamber 16 is surmounted by a perforate floor 18 representing the lower surface of the vault 12. Within the inner chamber of the vault and resting upon floor 18 are a series of steel mesh cages 20a-20d. Each of these cages 20a-20d has an upwardly disposed opening (not shown) within which the solid waste is dumped. The cages then are maneuvered, for example, by an overhead hoist, shown generally at 22, into the positions schematically represented in the figure. A supply of dry sand also is provided within the chamber of the vault in sufficient quantity such that when plenum 16 receives hot atmospheric air from along conduit 24, each of the cages 20a-20d will be immersed in a fluidized bed of hot sand and air. Inasmuch as this sand has a relatively high specific heat characteristic, a considerably enhanced drying procedure minimizing both residence time for drying as well as assuring complete drying is provided. Following a predetermined residence interval within vault 12, the cages are removed and the waste contained therein is transported to a covered or suitably protected storage area such as a building or the like, as is represented by block 26. The sand utilized at stage 10, for the most part, remains thereat due to the nature of the fluidized bed. However, the minor amount of sand carried with the dried material as well as sand initially present in the waste either falls therefrom during interstage movement or harmlessly passes through the process as inert material. Because the solid waste material now is in a substantially dry state, such storage becomes practical, inasmuch as biodegradation of the waste requires a moisture input. Accordingly, maliferous odors normally encountered with the storage of solid wastes are substantially eliminated with the procedure. Of course, such storage is temporary and useful for assuring a continued steady input delivery rate of solid waste to the conversion components of the system. In this regard, from protected storage 26, as represented by the downwardly directed arrow, substantially dry solid waste is deposited within a lock hopper 28. Hopper 28 is intermittently pressurizable such that it will depressurize to receive waste from storage 26, then become pressurized for purposes of introducing the received waste into the system. Accordingly, upon being brought to atmospheric pressure, hopper 28 is secured and pressurized, following which duct valve 30 is opened to permit the passage of waste through duct 32 into a next succeeding feed hopper 34. Feed hopper 34 is continuously maintained at the operational pressure of the system and serves to provide for the insertion of a steady and predetermined rate of solid waste through duct 36, as regulated by valve 38, to hydrogasification reactor 40. As described in the above-noted U.S. Pat. No. 4,005,994, reactor 40 comprises an elongate confined zone under pressure, for example about 18 atmospheres. Hot hydrogen-containing synthesis gas is introduced into the lowermost region of the confined zone of reactor 40 through a feed gas distribution ring 42 encircling the zone which is fed from synthesis gas input line 44. Accordingly, as shredded, substantially dried waste enters the upper region of the confined zone of reactor 40 from duct 36, it encounters upwardly rising hot synthesis gas in countercurrent fashion and, additionally, is selectively delayed in its gravitationally induced descent by baffles as at 46.

The total residence time for the organic material moving in countercurrent fashion through the confined zone of reactor 40 is substantially lessened with the instant arrangement. Because the material is substantially dry before entering reactor 40, very little time, and, therefore, transit distance is required to remove final moisture. Thus, the material is quickly made capable of reacting with synthesis gas to produce a methane-containing product gas. The interval required in the latter reaction is quite short, being measured in seconds and, of course, will depend upon the pressure and temperature as well as hydrogen content of the synthesis gas utilized. The result of the arrangement is to considerably reduce the necessary length of the confined zone of reactor 40.

More conventionally, undried waste would be acted upon in three stages; first, all moisture is removed by virtue of the waste commingling with hot synthesis gas; next, the organic components of the waste react with the synthesis gas to produce a methane containing product gas. Then, as the organic waste continues to progress through the reaction zone, it is converted to a carbon-containing char. Inorganic materials, for instance, aluminum, steel, glass and the like pass somewhat directly by gravity through the elongate reactor zone and, during such transit are sterilized by the heat encountered with the synthesis gas. Note, that for the embodiment shown, the temperature within reactor 40 will vary from about 1000° at the point of feed 42 of the synthesis gas, to a relatively lower temperature at the uppermost region of the reactor zone. These temperatures, however, are not so high as to deleteriously affect the waste material. For example, the glass materials are not sintered and the metallic components are not oxidized nor fused with the glass components.

Both the inorganic waste components and the char developed pass from reactor 40 by gravity and into duct 48 leading toward a quench tank 50.

As the char and sterilized inorganic designated components of the waste pass by gravity through duct 48 they encounter an aspirator represented schematically by a steam input line 52 and a delivery conduit 54 leading to a gasification reactor 56. With this aspiration arrangement, the lighter char is delivered to reactor 56, while heavier inorganic waste materials drop to the liquid contained within quench tank 50. This inorganic waste may then be removed through duct 58 and valve 60 as a slurry for further processing as a valuable by-product.

As the char and steam enter reactor 56 from conduit 54, oxygen is additionally introduced through line 62 and under the noted pressure of about 18 atmospheres, the well known exothermic gasification chemical reactions occur to form a synthesis gas consisting essentially of carbon monoxide, carbon dioxide, hydrogen and a small quantity of water vapor. The synthesis gas exits from the gasification reactor 56 through input line 44 which conducts the same to the ring 42. Generally, all of the char is consumed in this reaction, however, any residue may be removed from reactor 56 through duct 64 as controlled by valve 66. Improvement in the performance of reactor 56 may be achieved by incorporating within the confined zone thereof a particulate, inert, non-abrading and thermally stable material such as alumina. This material becomes distributed throughout the zone of reaction and the inert particles thereof tend to improve the distribution of char within the zone permitting it to move randomly through a tortuous path. The inert particles also tend to evolve a constant temperature within the zone thus improving its performance.

After the above described reactions in reactor 40, hot product gas under pressure and generally comprised of methane, ethane, CO, $CO_2$, $H_2$ and $H_2O$ exits through line 70, whereupon it is introduced to one side of a heat exchanger 72. At heat exchanger 72, a thermal exchange is provided with atmospheric air supplied through line 24 and deriving from a supply represented by block 76. The thus heated air, as above described, is introduced to plenum 16 of drying station 10 for use in developing the fluidized sand drying bed. Accordingly, the thermal energy of the product gas is utilized in an earlier stage 10 of the overall process to derive greater efficiencies at the hydrogasification stage 40 of the system.

Product gas exiting from heat exchanger 72 may be conveyed via line 74 to a scrubber 78 where, in conventional manner, particulate material and a small quantity of $CO_2$ is scrubbed therefrom. Additional $CO_2$ may be removed following scrubbing and, if desired, carbon monoxide may be methanated following scrubbing by reacting it with hydrogen in the presence of a catalyst. Inasmuch as the carbon monoxide is present in relatively low amounts, essentially all of which is readily methanated, it is not necessary to convert some of it to $CO_2$ by the water gas shift reaction. From scrubber 78 and following possible methanation, clean product gas is conveyed via line 80 to ultimate usage or insertion into a distribution system, such general utilization being depicted by block 82. Methanation is an optional stage with the instant system, inasmuch as waste exhibits a low sulfur content. Accordingly, following removal of particulate matter, the gas may be utilized directly as a fuel gas for industrial purposes. Based upon cost per B.T.U., such fuel is much less expensive than the substitute natural gas formed by methanation.

Scrubber 78 utilizes a water supply represented by block 84 and coupled into the scrubber through line 86. Disposal of liquid by-products of the scrubbing operation is provided through duct 87 and associated valve 88.

Figure 2:
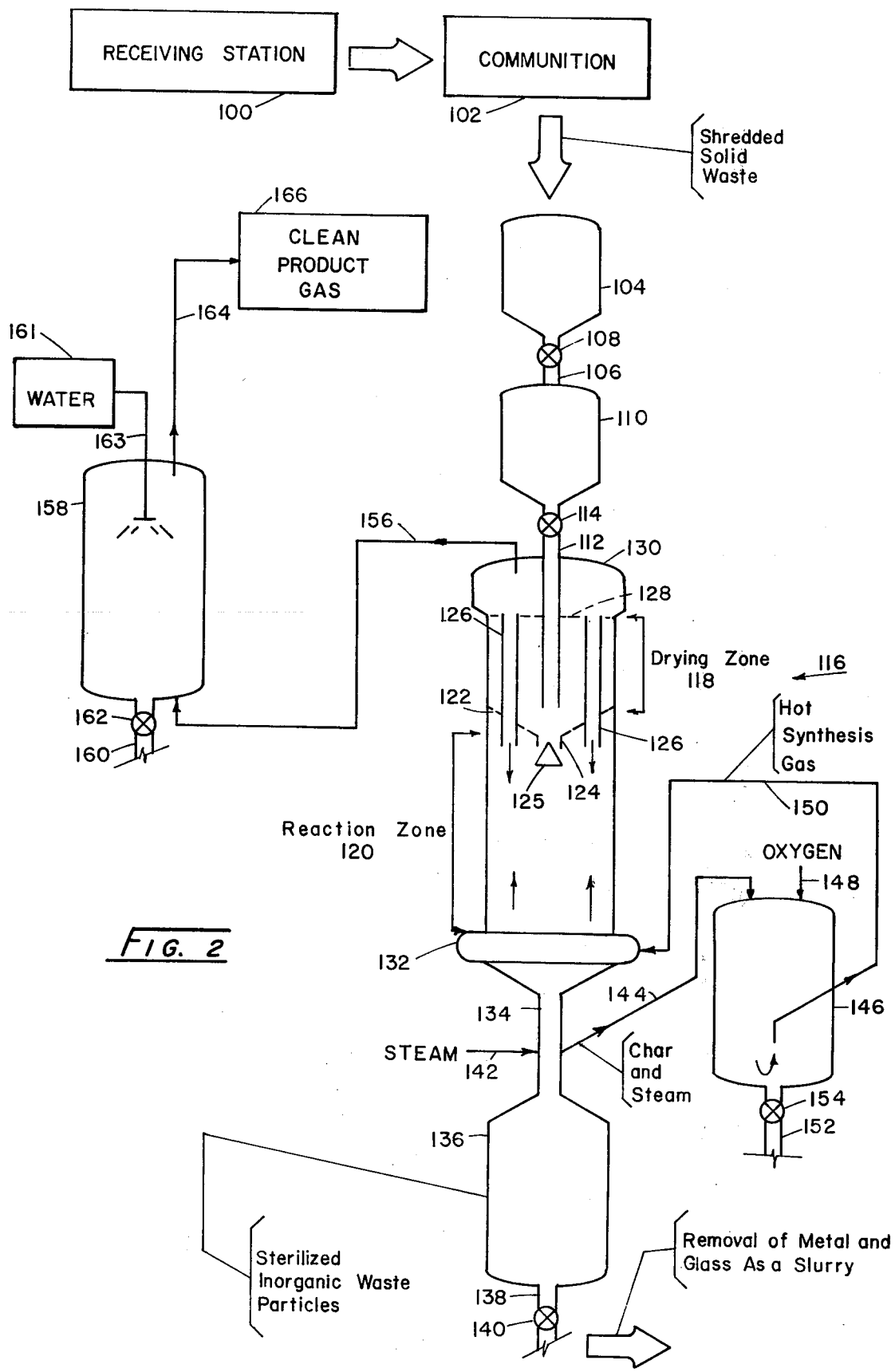
FIG. 2 is a non-scale, schematic system and process flow diagram of another aspect of the invention.

Referring to FIG. 2, another embodiment of the invention is schematically revealed. As represented at block 100, solid waste is delivered to a receiving station for short interval inventory and subsequent movement to a comminution stage represented by block 102. Stations as represented at 102 are conventional in the art and, generally, are provided as a hammer mill which operates to alter the average particulate size of the waste to a more manageable dimension. From comminution stage 102, the shredded waste is introduced to a lock hopper 104. As before, hopper 104 is of a variety which is intermittently de-pressurized for purposes of receiving comminuted or shredded waste at atmospheric pressure and subsequently undergoes pressurization to system levels. From lock hopper 104, the shredded waste moves through duct 106, as controlled by valve 108, to a feed hopper 110. Hopper 110 is continuously maintained at the elevated pressure of the system, i.e. about 18 atmospheres, and serves to progressively feed the solid waste through duct 112 at a rate controlled by valve 114. The material exits from duct 112 within the interior of hydrogasification reactor 116.

Reactor 116 is configured to define two distinct confined and pressurized zones, an upwardly disposed drying zone, represented generally at 118, and a contiguous, lower-disposed reaction zone 120. Positioned between zones 118 and 120 is a perforate gas distribution component 122. Component 122 is generally conically shaped and contains gas transfer openings as well as an outlet 124 centrally disposed at its lowermost portion. Additionally, positioned within drying zone 118 are collector conduits, as at 126, which extend from a position within reaction zone 120 to a predetermined level identified by dashed line 128 located at the uppermost region of drying zone 118. Note additionally, that the uppermost dome portion 130 of reactor 116 is formed having an enlarged cross-section to present a correspondingly enlarged volume and consequent pressure drop to gases moving thereinto.

With the arrangement, as shredded solid waste enters reactor 116 from duct 112, the more dense, inorganic components thereof drop to the lowermost portion of drying zone 118 at which location they are temporarily restrained from passage through outlet 124 of component 122 by plug 125. Plug 125 is intermittently released to permit the inorganic designated particles to pass outlet 124 and confront hot synthesis gas moving upwardly by virtue of the entry thereof at the lowermost portion of reaction zone 120 through a distributor 132. In consequence, these particles are dried and sterilized, whereupon they pass into lower duct 134 and thence into quench tank 136. At tank 136, the particles are immersed in water and cooled. Accordingly, the inorganic components may be removed from duct 138 as a water slurry for further separation and treatment by actuation of a valve 140. It may be noted that the utilization of the comminution feature at station 102 serves to maintain the particles of inorganic waste at an appropriate size for this purpose. Particularly, glass particles will be fractured and in relatively small size for simplified removal and separation.

Returning to the operation of reactor 116, the organic designated waste particles passing through duct 112 initially will exhibit a moisture content and, in this more dense form, collect in the region of the upper surface of perforate gas distribution component 122. However, hot product gas from reaction zone 120 will be passing through component 122 to effect a progressive drying of those particles. As this drying interaction continues a random movement of the particles ensues, the lighter, i.e. dryer, particles generally migrating toward upper level 128 of drying zone 118. When substantially dry, a greater proportion of the particles will reach the uppermost region, gas velocity thereat being lower, and the particles will tend to migrate into the upper entrances of collector conduits 126. Thereupon the particles drop into reaction zone 120 to react with synthesis gas and form product gas and char. Plug 125 serves to maintain the liquid-like bed of particles within zone 118 for a predetermined batch interval. As in the embodiment of FIG. 1, the char exits through duct 134, whereupon it is separated from inorganic waste components by an aspiration arrangement including steam input 142 and conduit 144.

With the arrangement shown, the relatively short residence time required within reaction zone 120 to produce product gas and char requires a vertical length for reaction zone 120 of relatively short extent. By comparison, the interval required to carry out drying within zone 118 is substantially greater. Through the use of gas distribution component 122, the organic waste material requiring drying is retained within drying zone 118 for the relatively lengthy residence interval without resort to a long drying zone configuration. Only when such moisture is removed will the organic waste enter conduits 126 for movement into reactive commingling with synthesis gas.

As in the earlier embodiment, synthesis gas is generated in a gasification reactor 146 by the introduction thereinto of char and steam through conduit 144 and oxygen through input line 148. The hot synthesis gas is removed via gas output line 150 for insertion at the lower region of reaction zone 120 through distributor 132. As before, substantially all of the char is consumed in the gasification reactor 146, however, any residue which may develop is removed through duct 152 by actuation of valve 154. Improvement in the performance of reactor 146 may be achieved by incorporating within the confined zone thereof a particulate, inert, non-abrading and thermally stable material such as alumina. This material becomes distributed throughout the zone of reaction and the inert particles thereof tend to improve the distribution of char within the zone permitting it to move randomly through a tortuous path. The inert particles also tend to evolve a constant temperature within the zone thus improving its performance.

Hot product gas is drawn from the upper dome portion of reactor 116 through line 156, whereupon it is introduced to scrubber 158. Scrubber 158 operates in conventional fashion, having a water input from source 161 and line 163 which serves to remove entrained organic liquids and particulate matter as well as sorb a small amount of $CO_2$. Liquid waste is removed from scrubber 158 through duct 160 by appropriate manipulation of valve 162. The clean product gas output from scrubber 158 is present at line 164 and is directed following optional methanation, for distribution, as represented at 166. As in the above embodiment, where industrial use is contemplated, the low sulfur content of waste permits a direct insertion of the product gas as fuel gas following removal of particulate matter and without methanation.

Inasmuch as the thermal energy of the product gas developed in reaction zone 120 is utilized for drying purposes at zone 118, the final temperature of the gas as it reaches dome 130 and output line 156 is considerably reduced. For example, during the drying phase at zone 118, thermal energy is utilized to accommodate for the heat of vaporization characteristic of the organic waste. Assuming temperatures in the range of about 1000° F. at the region of distributor 132, the temperature ultimately developed in drying zone 118 will be in the range of about 300° F. The system represented in FIG. 2 also may utilize a preliminary waste drying station as described at 10 in the embodiment of FIG. 1. This additional step would provide a lesser degree of drying. However, depending upon the installation at hand and waste characteristic, it may be found to improve system efficiency. As before, the thermal energy of gas within output line 156 would be exchanged with an input of atmospheric air at an exchanger station, whereupon the heated air is delivered to the drying station. Predrying may be found to facilitate the physical movement of the waste.

Figure 3:
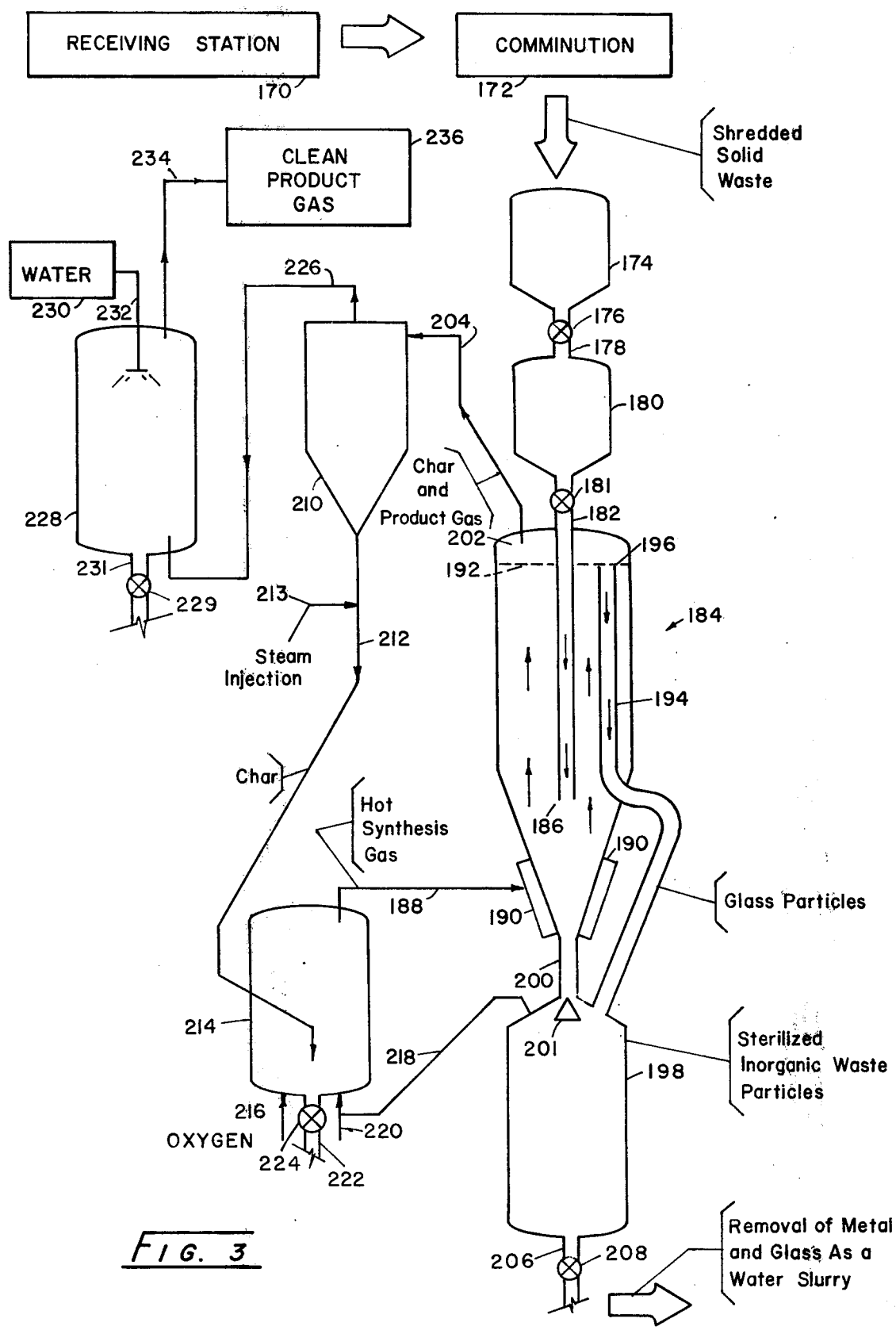
FIG. 3 is a schematic, non-scale system and process flow diagram of still another embodiment of the invention.

Turning now to FIG. 3, another arrangement of the invention is revealed. In the figure, a receiving station for collecting solid municipal refuse and the like is represented at block 170. Waste accumulated at station 170 is moved to a comminution stage 172 which, as indicated earlier, may be present as a hammer mill or conventional shredding device. For the instant embodiment it is important to note that the comminution stage 172 serves to fracture frangible inorganic components, particularly glass. In consequence, all such glass particles are of very small dimension. The shredded or comminuted solid waste is moved in increments from stage 172 and inserted into lock hopper 174 at atmospheric pressure. Following such insertion, the hopper 174 is closed and pressurized, whereupon valve 176 is opened to permit the passage of shredded solid wastes through duct 178 into feed hopper 180. Hopper 180 serves to provide a continuous supply of comminuted solid waste which is passed at a rate predetermined by valve 181, through duct 182 to the confined pressurized zone of a hydrogasifying reactor shown generally at 184.

Reactor 184 is configured in unitary elongate form and is fed from the outlet 186 of duct 182 positioned at a lower region of the zone. Hot synthesis gas under pressure is introduced to reactor 184 from line 188 through a plenum 190. The plenum 190 is positioned below outlet 186 of duct 182. Gas enter the confined zone of the reactor at such pressure and rate as to develop a fluidized bed of hot gas, organic particulate matter and fractured inorganic particles, more particularly, glass fragments. The fluidized bed is isothermal and extends upwardly to a predetermined level as identified by dashed line 192. Also extending within the confined zone of reactor 184 is a collector conduit 194 having an opening 196 situate at the predetermined top level 192 of the fluidized bed. The opposite end of collect or conduit 194 extends to quench tank 198 as does an output duct 200 which communicates with the lowermost level of the conicially shaped lower region of the confined zone of reactor 184. A plug 201 is positioned within duct 200 for purposes of assuring the establishment of a fluidized bed. This plug is intermittently released to permit the movement of heavy inorganic waste into quench tank 198. Without plug 201, non-fluidized crushed glass components will tend to fall through duct 200. Thus configured, as comminuted waste particles are expelled from opening 186 of duct 182, the heavy metal components therewithin are heated in the lower region of the reactor zone and, when plug 201 is actuated to open duct 200, dropped into quench tank 198. The synthesis gases released from plenum 190 commingle both with organic waste components such as paper and the like as well as the small particulate inorganic matter earlier fractured at comminution stage 172. Thus, there is commingled along the length of the confined zone of the reactor 184 a combination of silica containing components of high specific heat and organic designated waste material. This lighter organic material is entrained within the fluidized bed and migrates upwardly, randomly colliding with glass particles to define a somewhat tortuous path and consequent desired drying residence time. The waste material progressively dries within the fluidized bed and emerges at upper level 192 as char. As the organic material becomes dry, a condition which is achieved in the vicinity of upper level 192, gasification reaction occurs to produce product gas accumulating in the dome-shaped upper region of the reactor zone at 202. The gas flow establishing the fluidized bed is of such intensity that product gas and char are expelled from the confined zone through conduit 204. Simultaneously, those inorganic designated particles, i.e. glass fragments and the like, which reach the top of the fluidized bed at level 192 are collected at opening 196 of collector conduit 194 for deposition within quench tank 198. As before, the inorganic material deposited in tank 198 from conduit 194 and duct 200 may be removed therefrom as a water slurry through duct 206 by appropriate actuation of valve 208.

With the fluidized bed arrangement shown, a generally higher quality of product gas is evolved. For example, additional hydrogen generally is formed by any steam which enters into the confined zone. Steam at the temperature of the fluidized bed, i.e. about 1000° F., will not react with produced methane to form CO and $H_2$, but will tend to react with CO to produce $H_2$ and $CO_2$. At the higher temperatures encountered in different systems, i.e. in the range of 1700° F., steam tends to deleteriously break down the methane component of product gas.

Product gas and char at conduit 204 are introduced peripherally to a cyclone separator 210, at which point the char is removed and delivered along conduit 212 to gasification reactor 214. Here, the char reacts with oxygen introduced to the reactor from line 216, as well as steam developed from line 218 coupled with quench tank 198 and line 220, representing an optional independent source. To assure proper delivery of the char through conduit 212 to the pressurized reactor 214, steam is injected into the former, as represented by line 213. Improvement in the performance of reactor 214 may be achieved by incorporating within the confined zone thereof a particulate, inert, non-abrading and thermally stable material such as alumina. This material becomes distributed throughout the zone of reaction and the inert particles thereof tend to improve the distribution of char within the zone permitting it to move randomly through a tortuous path. The inert particles also tend to evolve a constant temperature within the zone thus improving its performance. As in the earlier embodiment, any residue developed within reactor 214 may be removed through duct 222 by appropriate operation of valve 224.

Product gas separated from the char in separator 210 is directed along conduit 226 to the input side of a scrubber 228. This injected gas confronts water sprayed through conduit 230 from source 232. The water serves to remove entrained organic liquids as well as particulate material. Liquid from the scrubber is removed through duct 229 by appropriate manipulation valve 231. As before, the gas may be further subjected to methanation by reacting it with $H_2$ in the presence of a catalyst. However, as noted above, direct industrial utilization of the gas without methanation may be provided following the removal of particulate material therefrom. The output of scrubber 228 is depicted coupled through line 234 to distribution system usage as represented at block 236. The system represented in FIG. 3 also may utilize a preliminary waste drying station as described at 10 in the embodiment of FIG. 1. This additional step would provide a lesser degree of drying than contemplated in the embodiment of that figure. However, depending upon the installation at hand as well as the characteristics of the waste which is treated, the added stage may be found to improve overall system efficiency. As before, the thermal energy of gas within output lines 204 or 226 would be exchanged with an input of atmospheric air under pressure at the heat exchanger station. The heated air thus generated then is delivered to the drying station. Such predrying may be found to facilitate the physical movement of the waste during initial stages of the treatment process.

Figure 4:
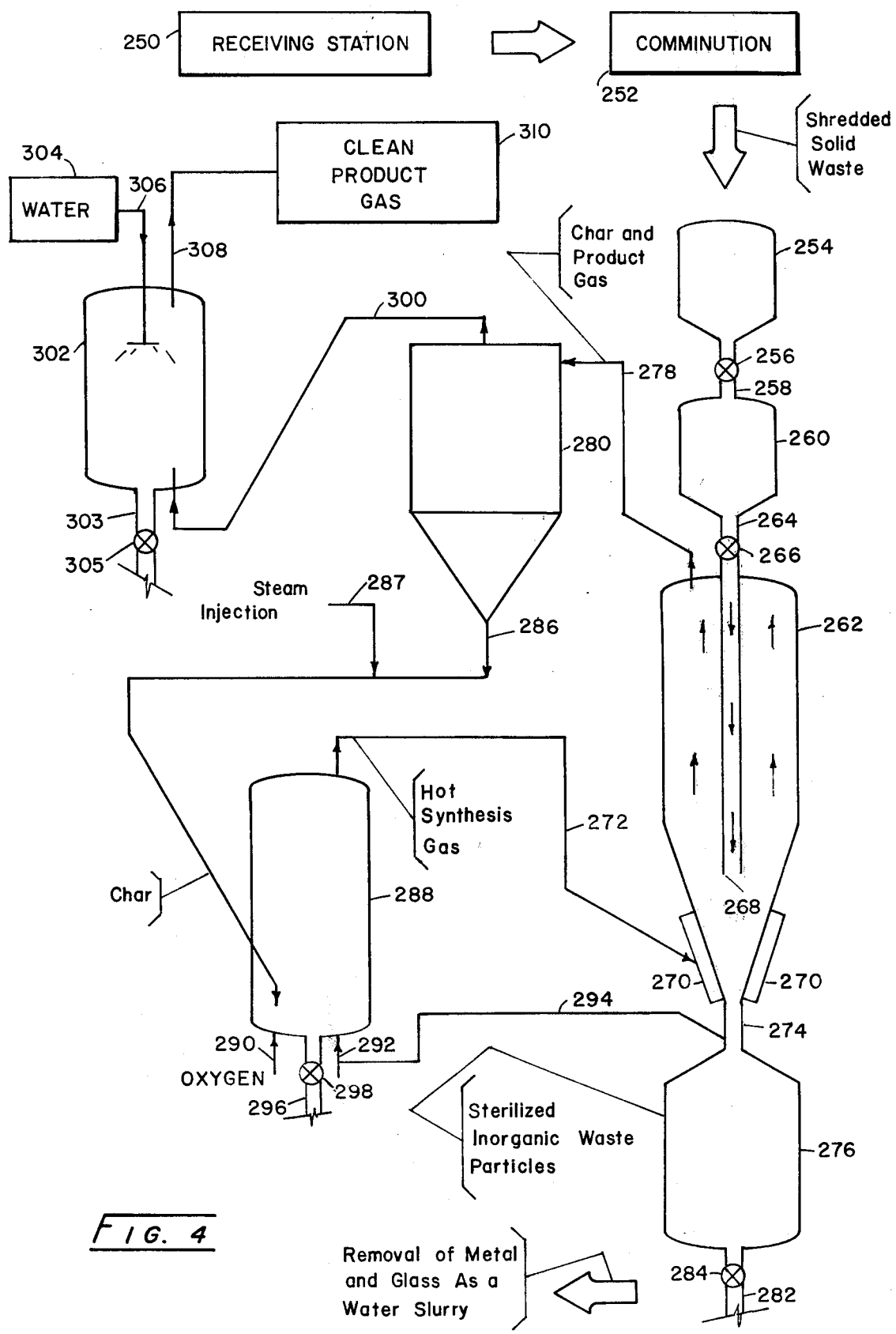
FIG. 4 is a non-scale system and process flow diagram of still another embodiment of the invention.

Turning now to FIG. 4, another version of the invention is schematically revealed. As before, the figure shows a receiving station, represented by block 250, which facility serves as the collection point for solid municipal waste. Major waste components which cannot be processed, for instance appliances and the like are picked from the waste at this point, whereupon it is transported to a comminution stage represented by block 252. The average particle size of the waste being reduced to a predetermined level, the comminuted solid waste is introduced to lock hopper 254. Hopper 254 receives the solid shredded waste at atmospheric pressure and subsequently is pressurized to system pressure levels, whereupon valve 256 is actuated to permit passage of the waste through duct 258 into feed hopper 260. Feed hopper 260 continuously remains at system pressure and serves to provide a feed inventory of waste materials for delivery to hydrogasifying reactor 262 through duct 264. The uniform rate of delivery of this material is regulated by valve 266.

Duct 264 extends into the pressurized confined zone of hydrogasifying reactor 262 to an extent wherein its lower disposed opening 268 is positioned within the lower region of the zone. This lowermost region is conically tapered and surmounted by a plenum 270 which is fed hot synthesis gas from line 272. This gas is at a pressure and transfer rate such that waste materials of organic designation are entrained within the gas and travel in commingled relationship therewith upwardly toward the uppermost portion of the confined zone. Inorganic, heavier waste material falls from outlet 268 to pass through the lowermost portion of the zone for deposition through duct 274 into quench tank 276. As the entrained organic-designated waste particles move upwardly with hot synthesis gas, the moisture content thereof progressively is reduced following which product gas is evolved and char produced in the uppermost, relatively short-length region of the confined zone. Both the product gas and char are removed from the confined zone of hydrogasification reactor 262 through conduit 278 for further processing at cyclone separator 280. The inorganic designated components of the waste passing into quench tank 276 are removed therefrom, for example, as a slurry through duct 282 under the control of valve 284.

Char separated from the product gas at cyclone separator 280 is delivered via conduit 286 to gasification reactor 288, while oxygen is introduced thereinto through line 290 and steam from lines 292 and 294, the latter collecting such steam from duct 274 extending from quench tank 276. To assure proper delivery of the char through conduit 212 to the pressurized reactor 288, steam is injected into the former, as represented by line 287. Substantially all of the char introduced from line 286 is utilized within reactor 288, however, any residue collecting within the reactor may be removed through duct 296 as controlled by valve 298.

Product gas from cyclone separator 280 is removed through line 300 and delivered to the input of scrubber 302. Within scrubber 302, the product gas is confronted with a water spray emanating from supply 304 and conduit 306. As noted earlier, entrained organic liquids as well as particulate material is removed from the gas whereupon it exits from scrubber 302 through line 308. Liquid from the scrubber is removed through duct 303 by appropriate manipulation of valve 305. Methanation may be carried out in conventional manner for producing a clean product gas suited for network distribution, as represented at block 310. However, as noted above, direct industrial utilization of the gas without methanation may be provided following the removal of particulate material therefrom. Such utilization is available in view of the higher quality of gas developed with the system. The system represented in FIG. 4 also may utilize a preliminary waste drying station as described at 10 in the embodiment of FIG. 1. This additional step would provide a lesser degree of drying of the waste, however, depending upon the installation at hand as well as the characteristics of the waste available, may be found to improve system efficiency. Such efficiencies may be gained either in terms of thermal energy usage or in terms of improving the maneuverability of the wastes through the various stages of the process. As before, the thermal energy of gas within output lines 278 or 300 would be exchanged with an input of atmospheric air at an exchanger station, whereupon the heated air is delivered to the drying station.

As before, improvement in the performance of reactor 288 may be achieved by incorporating within the confined zone thereof a particulate, inert, non-abrading and thermally stable material such as alumina. This material becomes distributed throughout the zone of reaction and the inert particles thereof tend to improve the distribution of char within the zone, permitting them to move randomly through a tortuous path for more efficient conversion. The inert particles also tend to evolve a constant temperature within the zone thus improving its performance.

Figure 5:
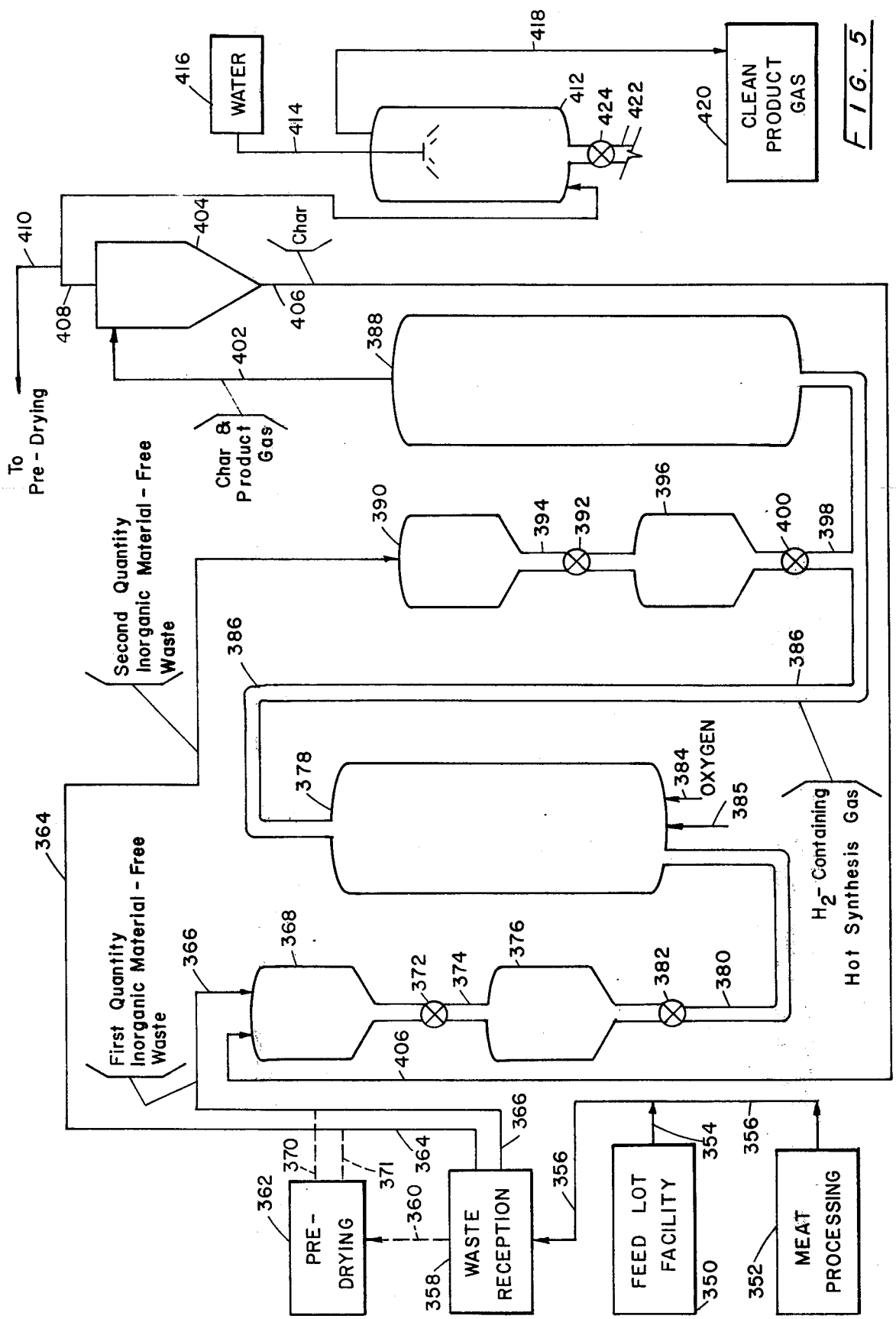
FIG. 5 is a schematic, non-scale system and process flow diagram of another embodiment of the invention wherein animal waste is converted to useful product gas.

Another embodiment of the invention is revealed in flow diagrammatic fashion in FIG. 5. This embodiment utilizes particular forms of feed material, to wit, solid waste which is substantially free of inorganic material as well as biomass materials. Such wastes are available in abundance as manure from feed lot facilities and the like. Where such facilities are integrated to provide a meat processing function in close physical association, the waste also will include such unused organic material as paunch manure and like by-products. Generally, the waste from the meat packing industry is developed in somewhat enormous quantities and heretofore has represented an environmental disposal problem. However, for the instant system, advantage is recognized in the utilization of such materials within a hydrogasification process. For instance, manure, as compared to solid municipal waste, is highly reactive, not being the subject matter of industrial processing as paper making wherein volatile products are removed. Further, the material is free of inorganic waste components thus permitting the utilization of higher reaction temperatures, inasmuch as the disadvantages occasioned through slagging of metal and glass are not encountered.

Looking to FIG. 5, a feedlot facility is represented by block 350. Such facilities are known to generate manure at rates of up to about 100 tons per day. Adjacent or integrated with the facility at block 350 may be a meat processing plant as represented at block 352. The waste output of the facilities represented at blocks at 350 and 352 is shown to be directed, respectively, along lines 354 and 356 to a waste reception function, represented by block 358. The waste collected at function 358 optionally may be subjected to predrying, as represented by dashed line 360 and function block 362. Such predrying may utilize the thermal energy developed in the ultimate product gas of the system, such gas being passed through a thermal exchange function wherein atmospheric air is heated and utilized in conjunction with a conventional drying process. From waste reception function 358, a first quantity of the waste is transported, as represented by lines 364 and 366, to lock hopper 368. Alternately, this first quantity of material may originate from predrying function 362 and may be transported, as represented by dashed lines 370 and 366 to hopper 368. Hopper 368 receives the waste at atmospheric pressure and, subsequently is secured and pressurized to initial system pressure levels. Upon pressurization, valve 372 is actuated to permit passage of the waste through duct 374 into feed hopper 376. Feed hopper 376 is continuously retained at the initial pressure of the system and serves to provide a feed inventory of the waste for delivery to the confined pressurized zone of a vertically oriented gasification reactor 378. Delivery of the material from hopper 366 is provided through duct 380 and the rate of delivery of the material is regulated by valve 382. Also introduced at the lower region of reactor 378 through line 384 is oxygen and, if desired, such amounts of steam through line 385 as may be desired at the determination of the operator. Within the confined zone of gasifying reactor 378, the oxygen confronts, commingles with and contacts the waste material introduced from duct 380. These components react at relatively high temperatures, for example in the range of about 1700° F. to about 1900° F. to produce hydrogen-containing synthesis gas and, possibly, char. Preferably, the confined zone of reactor 378 will contain a particulate, chemically inert, nonabrading and thermally stable material such as alumina which becomes distributed throughout the zone of reaction. These inert particles tend to improve the distribution of waste components and char within the zone, causing such waste and char to move through a more tortuous path and thus remain within the zone for an extended reaction residence interval. Of additional advantage, the inert particles tend to develop a constant temperature throughout the zone to improve the performance of the reactor.

Synthesis gas and ash exit from the confined zone of reactor 378 under the impetus of the relatively high pressures thereat through duct 386.

Duct 386 extends, in turn, to the lower region of the confined zone of a hydrogasifying reactor 388. Note, in this regard that reactor 388 is functionally coupled in series fashion with gasification reactor 378. Further, pressurization of the series-connected system progressively diminishes from the point of commencement of its operation to the end product. By so combining the reactors in series, a system which is more facilely operated is achieved. Simultaneously introduced to the confined zone of hydrogasifying reactor 388 through duct 386 is a second quantity of waste, transported from predrying function 362 through lines 371 and 364, or waste reception function 358 to lock hopper 390, as represented by line 364. Hopper 390 receives the waste at atmospheric pressure and, subsequently, is secured and pressurized to the pressure level extant at duct 386. Following such pressurization, valve 392 is selectively actuated to permit passage of the waste through duct 394 into feed hopper 396. Feed hopper 396 continuously remains at the system pressure of duct 386 and serves to provide a feed inventory of waste materials for delivery to hydrogasifying reactor 388 through ducts 398 and 386. The rate of delivery of this material is regulated by valve 400.

Within hydrogasifying reactor 388, the hot, hydrogen containing synthesis gas confronts, commingles with and contacts the waste material introduced from duct 398 into duct 386. Product gas and char is produced in consequence of this union. Preferably, in similar fashion as provided in the case of gasification reactor 378, the confined zone of hydrogasifying reactor 388 also will contain a particulate, inert, thermally stable and substantially non-abrading material such as alumina, which becomes distributed throughout the zone of reaction. These inert particles tend to improve the distribution of waste particles within the zone, causing such waste to move through a more tortuous path and thus remain within the zone for an extended reaction residence interval. With the multi-solid fluid bed system developed with the alumina particles, gas distribution is excellent and channeling phenomena are prevented. Solids plugging and bridging due to the fibrous nature of the solids is avoided by the agitation furnished through the fluidized alumina particles. Further, internal heat transfer to the waste material is greatly increased to enhance the hydrogasification rate. Of particular advantage, very high solid through-put rates can be achieved in view of the very high velocities that can be employed thereby reducing reactor investment. Additionally, the multi-solid fluid bed represents an effective heat sink which stabilizes the temperatures within a reaction zone against fluctuation otherwise encountered due to such parameters as feed compoistion and gas temperature. Finally, the residence times of lighter particles are substantially increased because of the collisions with the dense fluid bed particles.

The hydrogasification process then produces product gas rich in methane and char, which is conveyed from the reaction zone of reactor 388 through suitable output conduiting, represented by line 402. Line 402 introduces the product gas and char peripherally to a cyclone separator 404, at which point the char is removed, as represented at line 406. Preferably, the char is delivered, to the input of lock hopper 368, positioned at the commencement of the process. Thus conveyed, the char contributes to the development of hydrogen-containing synthesis gas at gasification reactor 378.

Product gas separated from the char in separator 404 exits therefrom along line 408. If desired, this product gas may be subjected to thermal exchange with atmospheric air for the earlier-described purpose of contributing to the pre-drying process at block 362. This option is represented by line 410. It should be understood, of course, that the methane rich gas tapped at line 410 also may be ignited to derive the thermal energy utilized in carrying out pre-drying step 362. The selection of the particular drying process generally will depend upon the relative proximity of the appropriate components of the facility as well as other conventional design considerations.

Conduit 408 is shown leading to the input side of a scrubber 412. When injected into scrubber 412, the gas confronts water sprayed through conduit 414 from source 416. The water serves to remove entrained organic liquids as well as particulate matter from the gas and, as before, the gas may be further subjected to methanation by reacting it with $H_2$ in the presence of a catalyst. However as noted above, direct industrial utilization of the product gas without methanation may be provided following the removal of particulate material therefrom. The output of scrubber 412 is depicted coupled through line 418 to distribution system usage, as represented at block 420. Liquid waste is removed from scrubber 412 through duct 422 by appropriate manipulation of valve 424.

Figure 6:
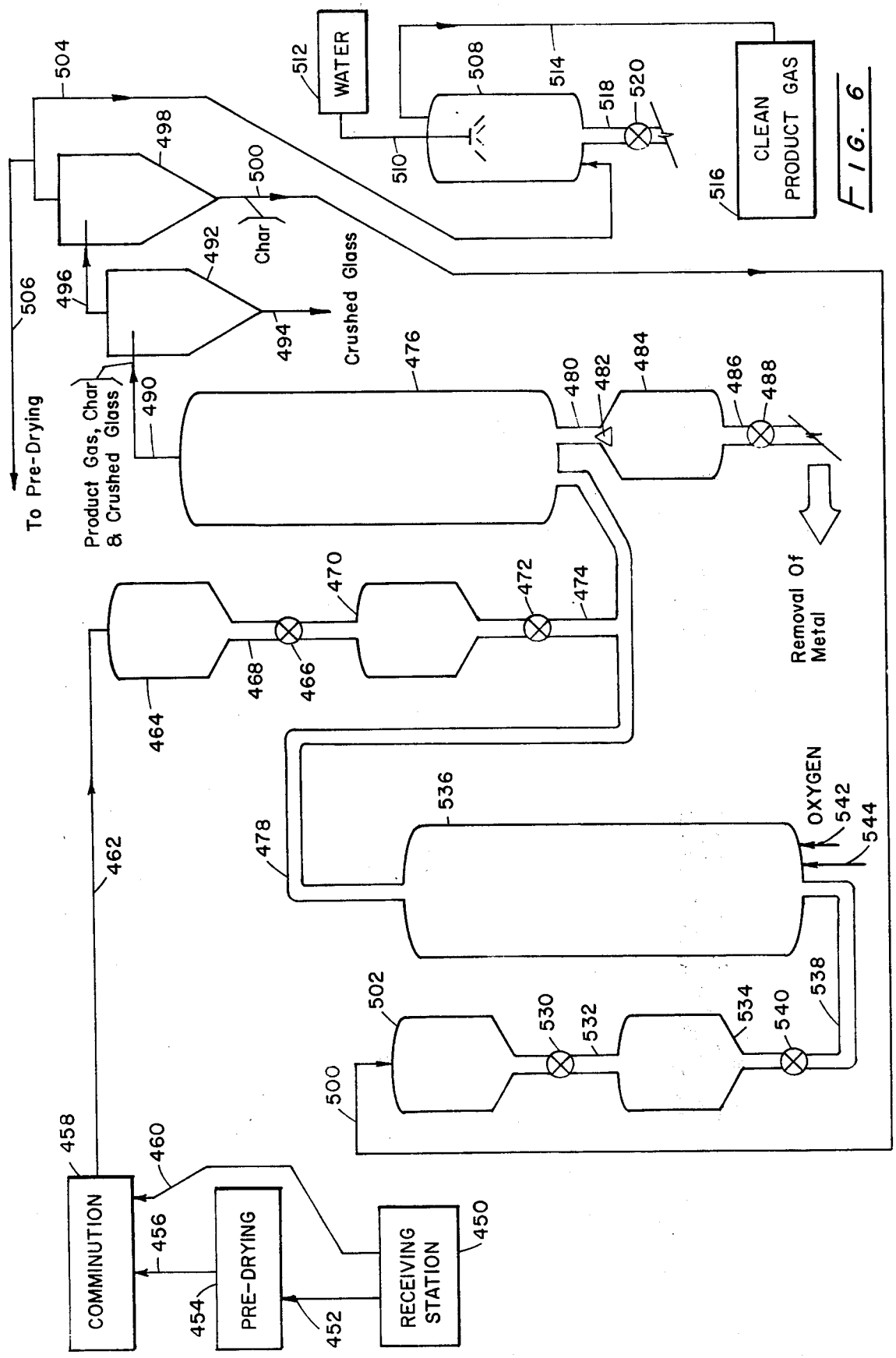
FIG. 6 is a schematic, non-scale system and process flow diagram of another embodiment of the invention wherein municipal waste is introduced to serially coupled gasification and hydrogasifying reactors to produce product gas.

Another embodiment of the invention is revealed in flow diagrammatic fashion in FIG. 6. This embodiment utilizes serially coupled hydrogasification and gasification reactor confined zones, similar to the arrangement described above in connection with the embodiment of FIG. 5. However, in the instant embodiment, conventional solid waste is treated to produce product gas, fluidized beds of chemically inert inorganic material such as alumina being established preferably in each of the confined zones and char being supplied to the gasification reactor following its removal from the continuous, pressurized flow of the process.

Looking to FIG. 6, a receiving station for collecting solid municipal refuse and the like is represented at block 450. Waste accumulated at station 450 is optionally moved, as indicated by line 452, to a predrying stage 454. At stage 454, heated atmospheric air is passed in contact with the waste to remove at least a portion of the moisture content thereof. From pre-drying stage 454, as represented by line 456, the waste is moved to comminution stage 458 which, as indicated earlier, may be present as a hammer mill or conventional shredding device. For the present embodiment, it is important to note that the comminution stage 458 serves to fracture frangible inorganic waste components, particularly glass. In consequence, all such glass particles are of very small dimension. Where the pre-drying stage 454 is omitted, waste from receiving station 450 is maneuvered directly to comminution stage 458, as represented by line 460. The shredded or comminuted solid waste is moved in increments from stage 458, as along a line 462, and inserted into a lock hopper 464. Following such insertion, the hopper 464 is closed and pressurized, whereupon valve 466 is opened to permit the passage of shredded solid waste through duct 468 into a feed hopper 470. Hopper 470 serves to provide a continuous supply of comminuted waste to the system which is passed at a rate predetermined by the valve 472 within duct 474 to the confined pressurized zone of a hydrogasifying reactor 476. Insertion into the reactor 476 is through a duct 478 which additionally carries hot hydrogen-containing synthesis gas generated at an earlier stage described later herein. The vertically oriented confined zone of reactor 476 preferably contains a quantity of particulate, inert and thermally stable material such as alumina. The particulate size of this material is selected such that a fluidized bed of those particles only and synthesis gas is established within the confined zone of reactor 476. Waste particles entering the zone through duct 478 confront this fluidized bed and the organic-designated components thereof as well as frangible inorganic components, i.e. glass particles, are entrained within the synthesis gas and move in a tortuous path defined by collisions with the inert particles of alumina until randomly reaching the upper level of the fluidized bed. From this level, fractured inorganic particles, i.e. glass, as well as char, and produced methane-containing gas are removed. Heavier inorganic materials are intermittently removed from the lowermost portion of the confined zone of reactor 476 through duct 480 upon an appropriate manipulation of a plug therein represented at 482. This removed inorganic material then passes through duct 480 to water within a quench tank 484. From quench tank 484, these larger principally metal, waste components are selectively removed through duct 486 by actuation of valve 488.

The use of a fluidized bed of inert particles such as alumina within the confined zone of reactor 476 tends to not only improve the distribution of waste particles within the zone through the noted development of a random tortuous path of entrained migration, but also, as discussed hereinabove, the bed provides an extended reaction residence interval as well as a constant temperature throughout the zone to improve reaction performance.

From the uppermost region of the confined zone of reactor 476, methane-containing product gas, char and glass or similar frangible fractured inorganic particles are removed through suitable output conduiting represented by line 490. Line 490 introduces the three component output peripherally to a cyclone separator 492, at which stage the more dense glass and similar frangible inorganic particles are removed, as represented at line 494. The char and methane rich product gas are removed from separator 492 through conduit 496 and introduced peripherally to a second cyclone separator 498. Within separator 498, char is removed and delivered along line 500 to the input of a lock hopper 502. Methane rich product gas is removed from separator 498 through conduit 504. If desired, this product gas may be subjected to thermal exchange with atmospheric air for the earlier-described purposes of contributing to the pre-drying process at block 454. This option is represented by line 506. It should be understood, of course, that the methane rich gas tapped at line 502 also may be ignited to derive the thermal energy utilized in carrying out pre-drying step 362. The selection of the particular drying process generally will depend upon the relative proximity of the appropriate components of the facility as well as other conventional design considerations.

Conduit 504 is shown leading to the input side of a scrubber 508. When injected into the scrubber, the gas confronts water sprayed through conduit 510 from a source represented at block 512. The water serves to remove entrained organic liquids as well as particulate matter from the gas and, as before, the gas may be further subjected to methanation by reacting it with $H_2$ in the presence of a catalyst. However as noted above, direct industrial utilization of the product gas without methanation may be provided following the removal of particulate material therefrom. The output of scrubber 412 is depicted coupled through line 514 to distribution system usage, as represented by block 516. Liquid waste is removed from scrubber 508 through duct 518 by appropriate manipulation of valve 520.

As noted above, char is removed from the system at conduit 500 and delivered to input of lock hopper 502 at atmospheric pressure. Following the delivery of a predetermined quantity of char to hopper 502, the hopper is secured and pressurized to initial system pressure levels. Upon pressurization, valve 530 is actuated to permit passage of the char through duct 532 into a feed hopper 534. Feed hopper 534 is continuously retained at the initial pressure of the system and serves to provide a feed inventory of char for delivery to the confined pressurized zone of a vertically oriented gasification reactor 536. Delivery of the char from hopper 534 is provided through duct 538 and the rate of delivery of the char is regulated by valve 540. Also introduced at the lower region of reactor 536 through line 542 is oxygen and, if desired, such amount of steam through line 544 as may be determined by the operator.

Within the confined zone of gasifying reactor 536, the oxygen confronts, commingles with and contacts the char introduced from duct 538. The components react to produce hydrogen-containing synthesis gas which is delivered through earlier-described duct 478 to hydrogasifying reactor 476.

Preferably, the confined zone of reactor 536 also will contain a particulate, inert and thermally stable material such as alumina which, under the influence of the oxygen introduced from line 542, and steam at line 544, develops a fluidized bed. As before, the inert particulate matter tends to improve the distribution of char within the confined zone causing the char to move through a more tortuous path and thus remain within the zone for an extended reaction residence interval. Of additional advantage, the inert alumina particles tend to develop a constant temperature throughout the zone to improve reactor performance.

It may be noted that gasification reactor 536 is serially coupled with hydrogasifying reactor 476 by virtue of connecting conduit or duct 478. This serial interrelationship of the reactors tends to provide for more efficient performance of the system.

Figure 7:
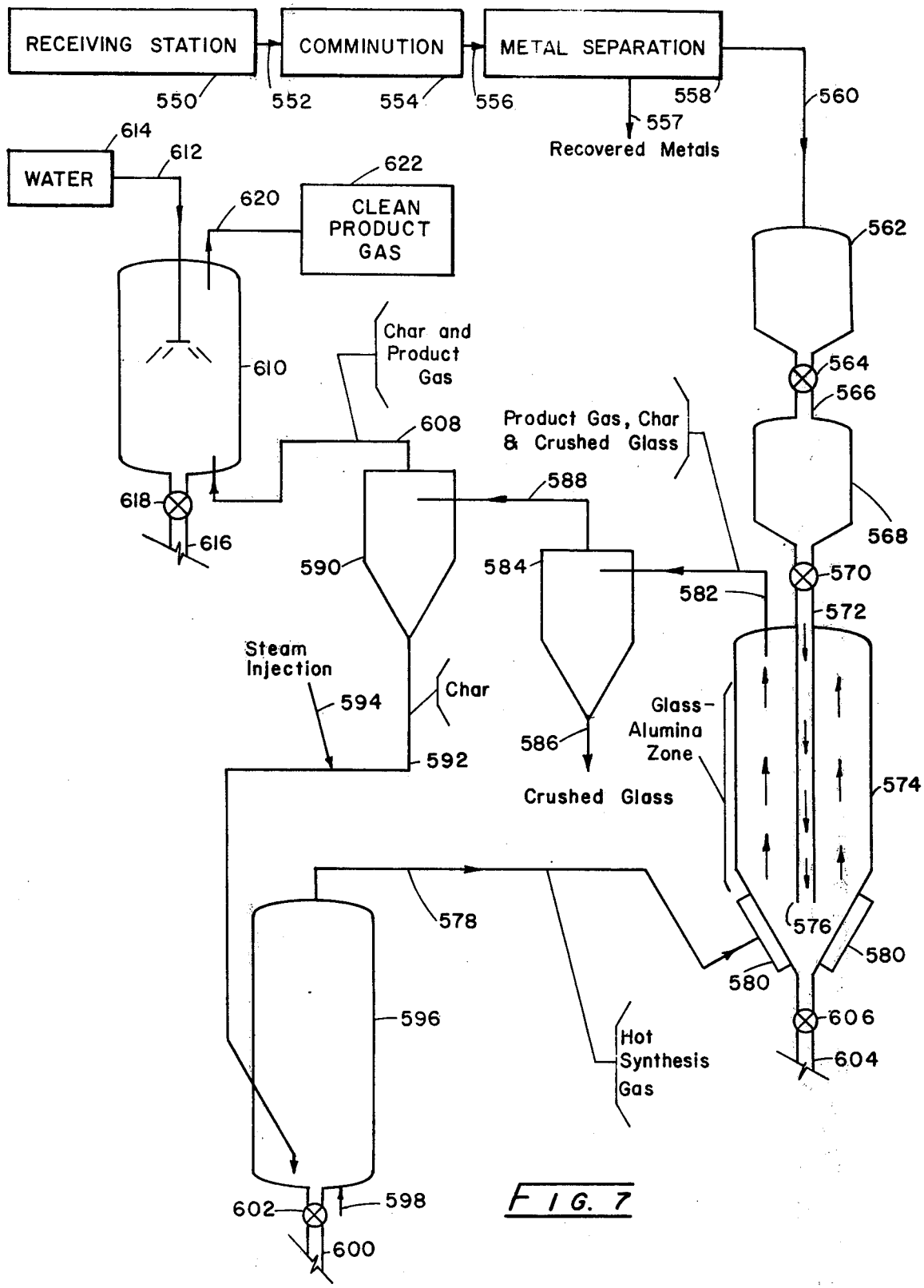
FIG. 7 is a schematic, non-scale system and process flow diagram of another embodiment of the invention wherein municipal waste is treated in conjunction with a fluidized bed of alumina particles within a hydrogasifying reactor.

The use of multi-solid fluid bed systems also is utilized in conjunction with the embodiment of FIG. 7. Looking to that figure, the system illustrated therein provides a receiving station as at 550 for collecting solid waste materials and/or biomass materials. Waste accumulated at station 550 is moved, as indicated by line 552, to a comminution stage 554. Optionally, the waste can be predried prior to or subsequent to, comminution using the techniques described earlier herein. Stage 554 may be present as a hammer mill or suitable shredding device. However, for the instant embodiment, stage 554 serves to fracture frangible inorganic waste components, particularly glass. In consequence, all such glass particles are of small dimension. From stage 554, the shredded waste is moved, as represented by line 556, to a metal separation stage, represented by block 558. At this stage, aluminum and ferrous metals are recovered from the waste such that the material passing from stage 558, as represented at line 560, includes fibrous organic matter as well as crushed glass. This material is moved in increments and inserted into a lock hopper 562. Following such insertion, the hopper 562 is closed and pressurized, whereupon valve 564 is opened to permit the passage of the material through duct 566 into a feed hopper 568. Hopper 568 serves to provide a continuous supply of waste materials to the system which is passed at a rate predetermined by valve 570 through elongate duct 572 into hydrogasifying reactor 574.

Reactor 574 is configured in unitary elongate form and is fed from the outlet 576 of duct 572 positioned at a lower region of the zone. Hot synthesis gas under pressure is introduced to reactor 574 from line 578 through a plenum 580. The plenum 580 is positioned below outlet 576 of duct 572. Also contained within the confined zone of reactor 574 is a quantity of a thermally stable non-abrading chemically inert particulate material such as alumina. Gas enters the confined zone of the reactor at such pressure and rate as to develop a fluidized bed of hot gas and alumina particles. The organic designated components of the materials fed from duct 572 migrate through this fluidized bed in combination with crushed glass particles. The alumina particles will tend to attrite the more brittle glass, allowing it to be elutriated with char evolved from the organic materials moving through the zone. Both the small glass particles and the char, in combination with product gas, pass from the reactor along conduit or line 582 to an initial cyclone-type separator 584. The crushed glass is removed by separation, as indicated by line 586, while char and product gas are conveyed along line 588 to a second cyclone separator 590. Separator 590 serves to separate the char from product gas and the former is delivered along line 592 in conjunction with the insertion or injection of steam, as represented at line 594, to the confined zone of a gasification reactor 596. Within reactor 596, the char reacts with oxygen introduced from line 598 as well as steam to produce hot synthesis gas which is removed from along line 578. As before, preferably, the confined zone of reactor 596 contains a chemically inert, non-abrading, thermally stable particulate material such as alumina which is subjected to oxygen flow to develop a fluidized bed for the purpose of improving reactor performance. As noted above, the char becomes distributed throughout the zone of reaction and the inert alumina particles tend to improve the distribution of char within the zone, improving residence intervals as well as providing a temperature control over the confined zone. Residues within reactor 596 may be removed therefrom through a duct as at 600 by manipulation of a valve 602. Similarly, residues developed within reactor 574 may be removed through duct 604 through manipulation of valve 606.

Product gas separated from the char in separator 590 is directed along conduit 608 to the input side of a scrubber 610. This injected gas confronts water sprayed through conduit 612 from a source 614. The water serves to remove entrained organic liquids as well as particulate material. Liquid from the scrubber is removed through duct 616 by appropriate manipulation of valve 618. As before, the gas may be further subjected to methanation by reacting it with $H_2$ in the presence of a catalyst. However, as noted above, direct industrial utilization of the gas without methanation may be provided following the removal of particulate material therefrom. The output of scrubber 610 is depicted coupled through line 620 to distribution system usage, as represented by block 622.

Since certain changes may be made in the above system and method without departing from the scope of the invention herein involved, it is intended that all matter contained in the above description or shown in the accompanying drawings shall be interpreted as illustrative and not in a limiting sense.

What is claimed:

1. A system for treating solid waste, biomass materials and the like, and converting said treated materials to methane-containing gas, comprising:

collection station means for receiving said materials said materials exhibiting a given initial moisture content;

dryer means for receiving said materials from said collection station means and subjecting them to heated atmospheric air to substantially reduce said initial moisture content thereof;

first means for transporting said materials from said collection station means to said dryer means;

storage means for retaining said dried materials under atmospheric pressure secure from atmospheric environmental effects;

second means for transporting said materials of reduced moisture content from said dryer means to said storage means;

receiving means for receiving quantities of said materials from said storage means, retaining them under elevated pressure and having an outlet for removing said materials of reduced moisture content under pressure;

third means for transporting said materials of reduced moisture content from said storage means to said receiving means;

a hydrogasifying reactor including first input duct means communicating between said receiving means outlet and a confined pressurized zone within said reactor for delivering said materials into said zone, second input duct means having an inlet for receiving hot synthesis gas and an outlet positioned for introducing synthesis gas exhibiting a given thermal energy to said zone at a lower region thereof, said zone being configured to commingle said synthesis gas and said materials for a predetermined residence interval to produce methane-containing gas of given thermal energy at a first output duct means and char and any inorganic designated waste at a second output duct means;

means coupled with said second output duct means for effecting the separation of said char from said inorganic designated waste;

a gasification reactor, including a confined zone, having an output coupled with said second input duct means for effecting said introduction of synthesis gas, input means coupled with said second output duct means for receiving water vapor and separated char in a condition substantially free of said inorganic designated waste, and means for supplying oxygen to said confined zone, said gasification reactor providing said synthesis gas;

means having an outlet for supplying a confined flow of atmospheric air;

heat exchanger means having a conduit coupled between said dryer means and said outlet supplying said flow of air, said conduit being situated to establish a thermal exchange relationship between gas derived from said hydrogasifying reactor first output duct and said atmospheric air for imparting a portion of said methane-containing gas thermal energy thereto and conveying heated said air to said dryer means.

2. The system of claim 1 in which said dryer means is configured for retaining said materials over a predetermined interval immersed within a fluidized bed environment of sand and said heated atmospheric air.

3. The system of claim 1 in which said receiving means comprises:

lock hopper means for receiving at atmospheric pressure quantities of said materials from said third transporting means and subsequently retaining said materials under elevated pressure; and feed hopper means having an input coupled with said lock hopper means for receiving said materials therefrom under said elevated pressure and retaining said materials under said elevated pressure, and including said outlet coupled in a pressure maintaining relationship with said hydrogasifying reactor first input duct means for passing said retained materials thereinto at a predetermined rate.

4. The system of claim 1 in which said gasification reactor is configured to retain a predetermined quantity of a chemically inert, thermally stable, substantially non-abrading particulate material.

5. A system for converting solid waste to methane-containing gas, comprising:

comminution means for comminuting said waste to provide organic components thereof having a given average particle size and fracturing frangible inorganic components thereof to a small average particle size;

receiving means for receiving quantities of said waste from said comminution means, retaining said received quantities under pressure, and having an outlet for removing said comminuted waste under pressure;

means for transporting said comminuted waste from said comminution means to said receiving means;

a hydrogasifying reactor including a confined zone under pressure, said reactor having first input duct means connected with said receiving means outlet, extending into said zone and having an outlet positioned at a lower disposed region thereof for delivering said waste thereinto, second input duct means having an inlet for receiving hot synthesis gas and an outlet positioned for delivering said hot synthesis gas at an outlet thereof into said zone at a location beneath said first input duct means outlet and at a pressure and flow rate selected to establish a fluidized bed of commingled said organic waste components and fractured inorganic waste components, said fluidized bed extending from said zone lower disposed region to a level predetermined to provide a residence interval of said organic waste components within said bed for removing moisture therefrom and subsequently reacting them with said synthesis gas to produce methane-containing gas and char, collector conduit means having an inlet opening disposed within said zone in the vicinity of said predetermined level for effecting removal of said fractured inorganic waste components from said zone at an outlet positioned remotely from said zone, first outlet duct means having an inlet communicating with said zone at a position above said predetermined level for effecting the removal of said produced methane-containing gas and char at an outlet remote from said zone and second outlet duct means having an inlet communicating with said zone lower disposed region at a position below said first input duct means outlet and having an outlet remote from said zone;

collection means coupled with said second outlet duct means outlet and said collector conduit means outlet for receiving said inorganic waste components;

separator means having an input coupled with said first outlet duct means outlet for separating said methane-containing gas from said char and having a first outlet for removing said methane-containing gas and a second outlet for removing said char;

a gasification reactor for producing said synthesis gas, having an output coupled with said hydrogasifying reactor second input duct means inlet, and input means for receiving said char, means for supplying oxygen to said gasification reactor; and means for delivering said char from said separator means second outlet to said gasification reactor input means.

6. The system of claim 5 in which the surface of said hydrogasifying reactor defining said zone is configured at the lowermost region thereof to slope toward said second outlet duct means.

7. The system of claim 5 wherein said collection means comprises quench tank means coupled with said collector conduit means outlet and said second outlet duct means outlet for receiving inorganic designated waste.

8. The system of claim 5 wherein said separator means comprises a cyclone separator.

9. The system of claim 5 in which said receiving means comprises:

lock hopper means for receiving at atmospheric pressure quantities of said waste from said comminution means and subsequently retaining said waste under elevated pressure; and feed hopper means having an input coupled with said lock hopper means for receiving said waste therefrom under said elevated pressure and retaining said waste under said elevated pressure, and having a said outlet coupled in pressure maintaining relationship with said hydrogasifying reactor first input duct means for passing said retained waste thereinto a a predetermined rate.

10. The system of claim 5 further including:

dryer means for receiving said waste prior to the said comminution thereof and subjecting it to heated atmospheric air to reduce the moisture content thereof;

means having an outlet supplying a confined flow of atmospheric air; and heat exchanger means having a conduit coupled between said dryer means and said outlet supplying said flow of air, said conduit being situated to establish a thermal exchange relationship between said methane-containing gas produced by said hydrogasifying reactor and said atmospheric air and configured to subsequently convey said air to said dryer means.

11. The system of claim 5 in which said gasification reactor is configured to retain a predetermined quantity of a chemically inert, thermally stable, substantially non-abrading material.

12. A system for converting solid waste to methane-containing gas, comprising:

collection station means for receiving said waste, said waste exhibiting a given moisture content and having organic and inorganic designated components;

receiving means for receiving quantities of said waste from said collection station means, retaining it under elevated pressure and having an outlet for removing said material under pressure;

a hydrogasifying reactor including an elongate confined, pressurized zone having a drying portion within an upwardly disposed region thereof and a contiguous reaction portion disposed therebeneath, a perforate gas distribution component extending across said zone and positioned intermediate said drying and reaction portions, said component having gas transfer openings therein through which methane-containing gas from said reaction region may pass at a predetermined rate of flow selected for effecting the progressive upward movement of said organic designated waste components to a predetermined upper level of said drying portion, said zone having a length to said level effective to cause the retention of said organic designated components within said drying portion for a residence interval sufficient to effect the removal of moisture therefrom;

first input duct means communicating between said receiving means and said elongate drying zone for transferring waste thereinto above and in the vicinity of said gas distribution component, said distribution component further including outlet means for effecting the direct movement of said inorganic designated waste components into said reactor portion, second input duct means for introducing synthesis gas exhibiting a given thermal enery to said elongate zone reaction portion, collector conduit means having at least one inlet situated proximate said level and extending therefrom into said reaction portion for collecting dried said organic waste components in the vicinity of said level and transferring them to said reaction portion, said reaction portion being configured to commingle said synthesis gas and said dry organic designated waste components for a predetermined residence interval to produce said methane-containing gas and char, first output duct means for removing said methane-containing gas from said elongate zone drying portion, and second output duct means for removing said inorganic designated waste components and said char from said elongate zone reaction portion;

means coupled with said second output duct means for effecting the separation of char from said inorganic designated waste components;

a gasification reactor having an output coupled with said second input duct means, first input means coupled with said second output duct means for receiving water vapor and separated char in a condition substantially free of said inorganic designated waste components, means for supplying oxygen to said gasification reactor, said gasification reactor comprising the source of said synthesis gas.

13. The system of claim 12 in which said gas distribution component is formed having a downwardly sloping surface, and said outlet means is prevent as an opening positioned centrally therewithin.

14. The system of claim 12 in which said hydrogasifying reactor is configured to support said elongate zone in a generally vertical orientation, the lowermost portion of which provides said reaction portion, said second output duct means being positioned beneath said reaction portion.

15. The system of claim 12 wherein said elongate zone drying portion is configured having a first cross sectional configuration from said predetermined level to said gas distribution component and a second cross sectional configuration above said predetermined level, said second cross sectional configuration having a greater area extent than said first cross sectional configuration.

16. The system of claim 12 further comprising:

dryer means for treating waste received at said collection station means by subjecting it to a flow of heated atmospheric air to reduce the moisture content thereof;

means having an outlet supplying a confined flow of atmospheric air; and heat exchanger means having a conduit coupled between said dryer means and said outlet supplying said flow of air, said conduit being situated to establish a thermal exchange relationship between said methane-containing gas produced by said hydrogasifying reactor and said atmospheric air and configured to subsequently convey said air to said dryer means, said receiving means receiving quantities of said waste of reduced moisture content.

17. The system of claim 12 in which said gasification reactor retains a predetermined quantity of a chemically inert, thermally stable, substantially non-abrading particulate material.

18. A system for converting waste material, biomass material and the like, said material being substantially free of inorganic components, to methane-containing gas, comprising:

collection station means for receiving said materials;

first receiving means for receiving first quantities of said material, retaining said received quantities under pressure and having an outlet for removing said material under pressure;

first means for transporting said materials from said collection station means to said first receiving means;

first duct means coupled with said first receiving means outlet for transferring said received material therefrom;

a gasification reactor including a confined zone under pressure and having an input communicating said first duct means with said zone for introducing into said zone said first quantities of material and means for introducing oxygen into said zone to produce hot synthesis gas, said reactor further including output duct means for transferring said hot synthesis gas;

second receiving means for receiving second quantities of said material and retaining said received quantities under pressure and having an outlet for removing said material under pressure;

second means for transporting said materials from said collection station means to said second receiving means;

second duct means coupled with said second receiving means outlet for transferring said material therefrom;

a hydrogasifying reactor including a confined zone under pressure, first input means communicating in direct series relationship with said gasification reactor by connection with said output duct means thereof for transferring said synthesis gas into said confined zone, second input means coupled with said second duct means of said second receiving means for transferring said second quantities of said material into said confined zone and effecting the commingling thereof with said synthesis gas within said zone to produce methane-containing gas and char, and outlet means for effecting the transfer of said methane-containing gas and char from said zone;

separator means coupled with said hydrogasifying reactor outlet means for separating said methane-containing gas from said char; and conduit means communicating between said separator means and said first receiving means for transferring said separated char to said first receiving means.

19. The system of claim 18 in which:
said gasification reactor is configured to support said zone thereof in a generally vertical orientation;
said gasification reactor input communicates with said zone at a lower disposed region thereof; and
said output duct means is coupled with said zone at an upwardly disposed region thereof.

20. The system of claim 19 in which:
said hydrogasifying reactor is configured to support said confined zone thereof in a generally vertical orientation;
said first and second input means communicate with said zone at a lower disposed region thereof; and
said outlet means is coupled with said zone at an upwardly disposed region thereof.

21. The system of claim 18 further comprising:
dryer means for subjecting said material to a flow of heated atmospheric air to reduce the moisture content thereof prior to its reception by said first and second receiving means;
means having an outlet supplying a confined flow of atmospheric air; and
heat exchanger means having a conduit coupled between said dryer means and said outlet supply in said flow of air, said conduit being situated to establish a thermal exchange relationship between said methane-containing gas produced by said hydrogasifying reactor and said atmospheric air so as to convey said air in a heated condition to said dryer means.

22. The system of claim 18 in which said gasification reactor confined zone is configured to retain a predetermined quantity of a chemically inert, thermally stable, substantially non-abrading particulate material.

23. The system of claim 22 in which said inert material is alumina.

24. The system of claim 18 in which said hydrogasifying reactor confined zone is configured to retain a predetermined quantity of a chemically inert, thermally stable, substantially non-abrading particulate material.

25. The system of claim 24 in which said material is alumina.

* * * * *